United States Patent
Kakita et al.

(10) Patent No.: US 6,855,555 B2
(45) Date of Patent: Feb. 15, 2005

(54) METHOD FOR SIMULTANEOUS ANALYSIS OF SACCHARIDE MIXTURE AND ANALYTICAL APPARATUS SYSTEM THEREFOR

(75) Inventors: Hirotaka Kakita, Kagawa (JP); Hiroshi Kamishima, Kagawa (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/327,125

(22) Filed: Dec. 24, 2002

(65) Prior Publication Data

US 2003/0129761 A1 Jul. 10, 2003

(30) Foreign Application Priority Data

Dec. 27, 2001 (JP) ........................................ 2001-398509

(51) Int. Cl.[7] .............................................. G01N 30/38
(52) U.S. Cl. ........................ 436/94; 436/95; 436/161; 436/164; 436/172; 422/70; 422/82.05; 422/82.08; 73/61.56
(58) Field of Search .......................... 436/94, 95, 161, 436/164, 172; 422/70, 82.05, 82.08; 73/61.56; 210/198.2, 656

(56) References Cited

U.S. PATENT DOCUMENTS 4,278,438 A 7/1981 Walraven

FOREIGN PATENT DOCUMENTS

JP     05-113439   * 5/1993

OTHER PUBLICATIONS

The Journal of Food Hygienic Society of Japan, vol. 39, No. 5, pp. 333–340 (1998).
Abstract Book for HPLC Kyoto (preprints in a meeting, Sep., 2001), pp. 135–136.
Patent Abstracts of Japan, vol. 014, No. 189 (P–1037), Apr. 17, 1990, Abstract of JP 02 035355 A, Feb. 5, 1990.
Patent Abstracts of Japan, vol. 006, No. 221 (P–153), Nov. 5, 1982, Abstract of JP 57 125349 A, Aug. 4, 1982.
Patent Abstracts of Japan; vol. 1998, No. 04; Mar. 31, 1998, Abstract of JP 09 318610 A, Dec. 12, 1998.
Patent Abstracts of Japan; vol. 2000, No. 22; Mar. 9, 2001, Abstract of JP 2001 13346 A, May 18, 2001.

* cited by examiner

Primary Examiner—Jan M. Ludlow
(74) Attorney, Agent, or Firm—Wenderoth, Lind & Ponack, L.L.P.

(57) ABSTRACT

In conducting liquid chromatographic analysis of a saccharide mixture containing monosaccharides and oligosaccharides, elution is conducted by using two kinds or more of mobile phases to separate the saccharide mixture into individual constituent saccharides followed by conversion thereof into corresponding derivatives by reaction with reagents and detection of the derivatives as contained in a detector cell. The method of the invention is characterized in that the detector cell is cleaned by washing with a cleaning solvent after completion of the detection of each of the saccharide derivatives. The invention also provides an apparatus for efficiently conducting the above-mentioned inventive method comprising an analytical column, a reactor for converting the separated constituent saccharides into the derivatives, detector cell for containing the derivative, a detector for detecting the derivative contained in the detector cell, a solvent-feed means to introduce a cell-cleaning solvent into the cell and a flow channel-switching means.

3 Claims, 5 Drawing Sheets

State (a)  State (b)

(9): from analytical column 9
(12): into reaction vessel 12
(13): into waste reservoir 13

METHOD FOR SIMULTANEOUS ANALYSIS OF SACCHARIDE MIXTURE AND ANALYTICAL APPARATUS SYSTEM THEREFOR

BACKGROUND OF THE INVENTION

The present invention relates to a method for simultaneous analysis of a saccharide mixture or, more particularly, to a method for the simultaneous analysis of a saccharide mixture including monosaccharides and oligosaccharides to be separated into individual constituents by means of the high-performance liquid chromatography as well as to an improved apparatus system used in the method.

As is known, conventional methods for the analysis of saccharides such as monosaccharides and oligosaccharides include the gel filtration method and normal-phase chromatographic method. It is a usual way in these methods that a differential refractometer is used for the detection of the component saccharides which do not emit fluorescence or do not exhibit absorption in the ultraviolet and visible ranges of light. Detection of monosaccharides and oligosaccharides is conducted also by using a differential refractometer.

The aforementioned analytical methods each have their respective disadvantages. For example, the gel filtration method is applicable to separation of monosaccharides from oligosaccharides but is not applicable to the separation between monosaccharides or between oligosaccharides having the same molecular weight without difficulties. In the normal-phase chromatographic method, the mobile phase is limited to have a single uniform composition, so that the method cannot be undertaken without sacrificing either completeness of elution of the oligosaccharides or separation among monosaccharides.

A further method is known for the simultaneous analysis of saccharides in which the sample mixture is subjected to a pre-treatment for conversion of the individual saccharides into their respective derivatives having characteristics for fluorescence emission or ultraviolet absorption followed by separation into the individual species by the high-performance liquid chromatographic method for detection by means of a fluorescence detector or ultraviolet absorption detector. This method is versatile in respect of the mobile phase which is not limited to a single composition but a plurality of mobile phases of different formulations can be employed for elution enabling separation among monosaccharides or among oligosaccharides to be advantageous as compared with the use of a single uniform mobile phase. This method, however, has a problem in the accuracy of the analytical results when the sample saccharide mixture contains a substance which influences on the yield of the reaction for conversion of a reducing saccharide into a derivative thereof. Accordingly, this method is not always satisfactory in respect of the quantitative accuracy when the method is applied to the high-sensitivity simultaneous analysis of reducing saccharides in a multicomponent sample such as foods.

Besides, a method is proposed in Japanese Patent Kokai 5-113439 and The Journal of Food Hygienic Society of Japan, volume 39, No. 5, pages 333–340 (1998), in which saccharides are separated by using two kinds or more of different mobile phases into component derivatives which are converted into their respective derivatives to be detected in a detector.

In these prior art methods, however, separation of the saccharides in an analytical column is followed by on-line admixing of the individual saccharides with a reagent for conversion of the same into their respective derivatives to be detected in a detector. It is accordingly unavoidable that the sample cells of the detector become stained during the analytical procedure by the reaction mixtures or the reagent solutions flowing through the cells resulting in an undesirable decrease in the detecting sensitivity, i.e. intensity of detectable fluorescence, as the number of the analytical runs increases.

It may be a natural countermeasure to solve the aforementioned problem of cell contamination to clean the detector cells after each of the analytical runs. This way of frequent cleaning of the detector cells, however, is not practical. Namely, cleaning of the detector cells must be undertaken in one of the following methods: (1) the analytical column is dismounted from the apparatus system and the pump is directly connected to the detector to introduce a cleaning solution to the cells, (2) the pump for mobile phase feeding is operated, without dismounting the analytical column, to feed the cleaning solvent; or (3) the cleaning solvent is fed by means of another pump connected to the analytical column at the outlet port of the eluate or downstream. These methods, however, have their respective disadvantages. For example, it is necessary in the first method (1) that the mobile-phase feed pump is turned off at least for a while for dismounting of the analytical column adversely affecting the accuracy for feed rate control and hence the accuracy of the analytical results. The second method (2) has a disadvantage that the cleaning solvent cannot be selected freely as limited by the material of the stationary phase filling the analytical column. The third method (3) has a problem that the cleaning solvent and the mobile phase are unavoidably intermixed more or less unless the mobile-phase feed pump is turned off during the cleaning treatment.

In addition, it is known that troubles are caused by a gas such as air originating in the solution or solvent used which stays in the pump to cause a decrease in the accuracy of flow rate control and hence a decrease in the reproducibility of the analytical results. It is sometimes the case that the air bubble enters the detector cell to disturb the performance of the detector. This problem is more serious when analysis is conducted continuously by using a mobile phase and a cleaning solution containing an organic solvent.

SUMMARY OF THE INVENTION

In view of the above-described problems and disadvantages in the prior art methods, the present invention has an object to provide a novel and unique method for the simultaneous analysis of a saccharide mixture capable of giving highly reproducible analytical results without a decrease in the detection sensitivity, i.e. the intensity of detectable fluorescence, of the respective saccharide derivatives and a decrease in the accuracy of flow rate control in the pump heretofore unavoidable as the number of analytical runs is increased by consecutively repeating the analytical procedures. The invention also has an object to provide an improved apparatus system used in practicing the inventive method.

Thus, the present invention provides a method for simultaneous analysis of a saccharide mixture which comprises the steps of;

separating a saccharide mixture containing monosaccharides and oligosaccharides into the individual constituent saccharides by a liquid chromatographic method using at least two different kinds of mobile phases;

reacting each of the thus separated constituent saccharides with a reagent to form a derivative thereof; and introducing the derivative into a detector cell where the derivative is detected by the detector, in which the detector cell used for detection is cleaned by washing with a cleaning solvent after each time of the analyses.

The present invention also provides an apparatus system for simultaneous analysis of a saccharide mixture which comprises the components of:

an analytical column of liquid chromatography for separating the saccharide mixture into individual constituent saccharides;

a reaction vessel for conversion of the separated saccharides into respective derivatives thereof;

a detector cell to which the derivatives of the separated saccharides are introduced;

a detector for detecting the saccharide derivatives contained in the detector cells mounted thereon;

a solvent-feed means for introducing a cleaning solvent into the detector cells after completion of detection or before next sample injection;

a regeneration means for re-equilibration of the analytical column; and a means for switching the flow channels of eluates out of the analytical column.

DETAILED DESCRIPTION OF THE PREFERRED EMBODIMENTS

The method of the present invention is a method for simultaneous analysis of a saccharide mixture containing at least one monosaccharide such as ribose, fructose and glucose and at least one oligosaccharide such as laminaribiose, laminaritriose, laminaritetraose, laminaripentaose, laminarihexaose and laminariheptaose, in which these constituent saccharides are separated each from the others for analysis. Examples of actual samples containing these monosaccharides and oligosaccharides include beverages such as malt drinks and fruit juices, confectionaries such as thickened malt syrups and jellies, foods such as honey and soy sauce, oligosaccharide products containing transgalactosylated oligosaccharide or isomaltoligosaccharide and others. The oligosaccharide here implied is a saccharide compound having a molecular mass not exceeding 5000.

In the method of the present invention, the saccharide mixture is separated into the individual constituent saccharides by a liquid chromatographic method using two kinds or more of mobile phases and each of the thus separated saccharides is reacted with one or more reagents to be converted into a corresponding derivative thereof, which is introduced into a detector cell. These steps of the method can be carried out, for example, according to the method described in Japanese Patent Kokai 5-113439.

Figure 1:
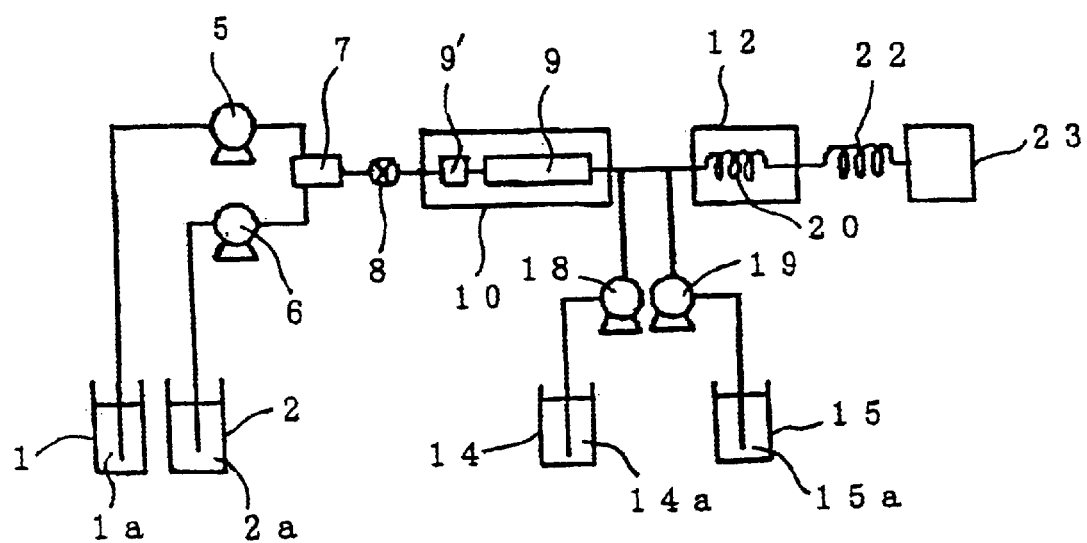
FIG. 1 is a partial flow chart of the inventive method showing the known part comprised therein.

FIG. 1 is an example of a flow chart showing a suitable apparatus system for practicing the above-described known portion of the inventive method. The high-performance liquid chromatography for separation of the saccharide mixture into constituent saccharides is conducted by using an analytical column for liquid chromatography filled with an adsorbent and at least two kinds of mobile phases.

The apparatus system of FIG. 1 comprises mobile phase reservoirs 1,2, pumps for constant-rate liquid feeding 5,6 and a mixer 7. When the method of gradient elution is undertaken, the mixer 7 is operated to mix the eluant 1a transferred from the mobile phase reservoir 1 by the pump 5 and the eluant 2a transferred from the mobile phase reservoir 2 by the pump 6. The sample solution injected to the system by way of a sample-injection valve 8 is introduced into the analytical column 9 by the eluant after passing a precolumn 9' for protection purpose to be separated there into the individual constituents. The precolumn 9' and analytical column 9 are kept at a constant temperature in the thermostat 10. The system also comprises reservoirs 14,15 of the reagents for conversion of the separated constituents into respective derivatives and constant-rate liquid feed pumps 18,19 for transfer of the reagents 14a,15a in the reagent reservoirs 14,15. It is usual that a plurality of reagent reservoirs are provided in order to facilitate replacement of the reagents in compliance with the constituents for conversion into the respective derivatives. Each of the constituent saccharides separated in the analytical column 9 is mixed with one or more reagents and converted into the derivative thereof while flowing through the reaction coil 20 in the reaction tank 12 followed by cooling in the cooling coil 22 and introduction into the detector 23 for detection. While the above description is given for a system having only two mobile phase reservoirs and two reagent reservoirs, it is of course possible to provide three or more of mobile phase reservoirs and three or more of reagent reservoirs to facilitate use of three kinds or more of eluants or reagents.

The aforementioned analytical column for liquid chromatography can be any one of those for ion-exchange chromatography, reversed-phase chromatography and normal-phase chromatography, of which the analytical columns for normal-phase chromatography are particularly preferable in respect of the applicability to the analysis of saccharides having a relatively large molecular mass ranging from 5000 to 10000 or even larger in consideration of the trend of proportionality between the saccharide retention power of the column and the molecular mass of the saccharide. The adsorbent to fill the analytical column for normal-phase chromatography can be a commercially available gel adsorbent such as TSKgel Amide-80 (trade name, a product by Tosoh Co.).

It is preferable in the method of the present invention that the feed rate of the solvent as the mobile phase is in the range from 0.2 to 1.6 ml/minute. Though dependent on the types of the analytical columns, the solvent as the mobile phase, when a normal-phase analytical column is used, is exemplified by binary solvent mixtures such as acetonitrile/water mixtures, acetone/water mixtures, 1,4-dioxane/water mixtures, methyl alcohol/water mixtures and ethyl alcohol/water mixtures and ternary solvent mixtures such as acetonitrile/methyl alcohol/water mixtures and acetonitrile/ethyl alcohol/water mixtures, of which acetonitrile/water binary mixtures are preferred.

It is optional that the above exemplified mobile-phase solvents are admixed with a salt such as ammonium formate, potassium dihydrogen phosphate and triethylamine acetate or a basic compound such as trihydroxymethyl aminomethane, ethanolamine and triethylamine. These additive salts or bases are added to the mobile-phase solvent in a concentration of around 10 mM with an object to improve sharpness of the elution peaks in the chromatograms.

While two kinds or more of different mobile-phase solvents are used in the inventive method, examples of suitable combination of the solvents include a 79:21 by volume acetonitrile/distilled water mixture and a 58:42 by volume acetonitrile/distilled water mixture. It is optional to conduct the chromatographic process by the step-wise elution method in which the proportion of the constituent solvents in the mobile phase is varied step-wise or by the gradient elution method in which the proportion of the constituent solvents is continuously varied.

The individual saccharide constituents separated in the liquid-chromatographic analytical column as described above are each on-line converted into a derivative thereof prior to entering the detector. The reagents used for conversion of the constituent saccharides into their respective derivatives are exemplified, for example, by ethylenediamine, ethanolamine, 2-cyanoacetamide, taurine, benzamidine, 4-methoxybenzamidine, phenol/sulfuric acid mixtures and aminobenzoic acids.

The derivative-forming reaction by using the above-exemplified reagents is conducted in a strongly alkaline condition when the reagent is 4-aminobenzoic acid, in a weakly alkaline condition when the reagent is ethylenediamine, ethanolamine, 2-cyanoacetamide, benzamidine or 4-methoxybenzamidine, in a neutral condition when the reagent is taurine and in a strongly acidic condition when the reagent is a phenol/sulfuric acid mixture. The amount of the reagent to be added should be deliberately selected for each of the constituent saccharides.

When the liquid-chromatographic analytical column used is a normal-phase chromatographic analytical column, in particular, the derivative-forming reagent is preferably selected from aromatic amidine compounds such as benzamidine and 4-methoxybenzamidine in consideration of their good solubility in the mobile-phase solvents for normal-phase chromatography and the high fluorescent intensity of the fluorescence-emitting derivatives as the reaction product formed even without addition of a borate buffer solution.

The detector used in the inventive method can be a fluorescence detector, ultraviolet absorption detector or visible light absorption detector although the types of the detectors and measuring wavelength for detection should be selected depending on the derivative-forming reagent and the mobile-phase solvent.

For example, a fluorescence detector is used with ethylenediamine as the reagent in the ion-exchange chromatography at an excitation wavelength of 360 nm and a measuring wavelength of 383 nm or 455 nm, a fluorescence detector is used with ethanolamine as the reagent in the ion-exchange chromatography at an excitation wavelength of 357 nm and a measuring wavelength of 436 nm, a fluorescence detector is used with 2-cyanoacetamide in the ion-exchange chromatography at an excitation wavelength of 331 nm and a measuring wavelength of 383 nm or an ultraviolet absorption detector is used with the same reagent in the ion-exchange chromatography, reversed-phase chromatography or ligand-exchange chromatography at a measuring wavelength range of 275–280 nm, a fluorescence detector is used with taurine in the ion-exchange chromatography at an excitation wavelength of 357 nm and a measuring wavelength of 440 nm, a fluorescence detector is used with benzamidine in the ion-exchange chromatography or normal-phase chromatography at an excitation wavelength of 288 nm and a measuring wavelength of 360 nm or 470 nm, a fluorescence detector is used with 4-methoxybenzamidine in the ion-exchange chromatography or normal-phase chromatography at an excitation wavelength of 310 nm and a measuring wavelength of 470 nm, a visible light absorption detector is used with a phenol/sulfuric acid mixture in the gel-filtration chromatography or ion-exchange chromatography at a measuring wavelength range of 480–490 nm and a visible-light absorption detector is used with 4-aminobenzoic acid in the reversed-phase chromatography at a measuring wavelength of 410 nm.

In addition to the above-described known steps of the analytical procedure, it is essential in the invention that the known procedure is followed by a unique step of cleaning the cell for containing the analytical sample, referred to as the detector cell hereinafter, equipped to the detector 23 by using a cleaning solvent after each time of completion of the detecting step of a single analytical sample.

The detector cell-cleaning solvent used here is exemplified by organic solvents such as acetone, acetonitrile, ethyl alcohol, methyl alcohol and isopropyl alcohol and acids such as nitric acid as well as distilled water. While the detector cell-cleaning solvent is preferably a solvent different from the mobile-phase solvent used in the chromatographic procedure, it is important that the cell-cleaning solvent is selected so as to accomplish a best cleaning effect depending on the types of the derivative-forming reagents and the saccharide samples.

The organic solvent as the cell-cleaning solvent should have a concentration preferably at least 85% by mass or, more preferably, at least 98% by mass. When nitric acid is used for cell cleaning, the concentration of the acid is preferably 2 to 6 molar. When the detector cell-cleaning solvent is immiscible with the sample solution in the detector cell, it is preferable that cleaning of the cell with the cell-cleaning solvent is preceded by replacement of the sample solution with a third solvent which is miscible with both of the sample solution and the cell-cleaning solvent. When the detector cell is to be cleaned by washing with a 2 to 6 molar nitric acid solution, for example, the washing treatment with the nitric acid is preceded and succeeded by washing with distilled water.

In conducting the cell-cleaning treatment in the inventive method, the washing procedure with the cell-cleaning solvent should be accompanied by replacement of the sample solution in the cell with a miscible solvent.

In conducting cleaning of the detector cell with the cleaning solvent, the solvent is introduced into the detector cell at a feed rate of 0.2 to 2.0 ml/minute although the viscosity of the cleaning solvent and pressure resistance of the detector cell must be taken into consideration in order to optimize the feed rate.

It is preferable in the inventive method to add the cell-cleaning treatment after completion of each analytical procedure for a single analytical sample although the frequency of insertion of the cell-cleaning treatments can be set to be after every sequence of several times of the analytical runs in consideration of the nature of the mobile-phase solvent, nature and concentration of the derivative-forming reagent, feed rate, reaction conditions, e.g., reaction time and reaction temperature, and other factors.

While the time taken for detector cell-cleaning in the inventive method can be freely selected in consideration of various factors including nature of the mobile-phase solvent, nature and concentration of the derivative-forming reagent, feed rate and reaction conditions, e.g., reaction time and reaction temperature, it is preferable, for example, that the cell-cleaning time is set in the range from 15 to 60 minutes at a feed rate of 0.6–2.0 ml/minute of a cell-cleaning solvent such as acetonitrile of at least 98% assay, acetone of at least 99% assay and ethyl alcohol of at least 99.5% assay with an analytical column for normal-phase chromatography as the liquid chromatographic analytical column and using an aromatic amidine as the derivative-forming reagent.

It is preferable that the detector cell-cleaning treatment in the inventive method is started only after a state is reached where the eluate from the analytical column no longer passes the detector cell by means of switching of the flow channels of the eluate from the analytical column. Passing of the eluate from the analytical column is resumed by switching the flow channels of the eluate from the analytical column during the interval from completion of the detector cell-cleaning treatment to the next injection of the sample solution.

In order to consecutively conduct the saccharide analysis by using two kinds or more of different mobile phases, it is necessary that completion of a run of analysis is followed by re-equilibration of the analytical column with the mobile phase used in the initial equilibration of the analytical column, i.e. the mobile phase used at the start of the analysis. Since it is not required in the inventive method to interrupt feeding of the solvent as the mobile phase to the analytical column even during proceeding of the detector cell-cleaning treatment, a continuous analytical procedure can be conducted under conditions to effect little variation of the feed rate. Further, the aforementioned re-equilibration treatment of the analytical column can be started already during proceeding of the detector cell-cleaning treatment so that the intermission between analytical runs in a consecutive analysis can be reduced.

It is usual that a degassing treatment to remove gases dissolved in the liquid is added in the inventive method before each of the mobile-phase solvent, reagent solution and cell-cleaning solvent enters the liquid-feed pump. It is, however, preferable or necessary that this degassing treatment of the liquid is omitted if the liquid to be degassed, e.g., 2-molar nitric acid, possibly attacks the materials forming the parts of the degasser coming into contact with the liquid phase or gaseous phase. This degassing of the dissolved gasses in the solvents or solutions has an object to prevent disturbing effects on the accuracy of the flow rate control in the liquid-feed pumps by the gas, e.g., air, originating in the solvent and on the detection in the detector cell by the entering gas bubbles.

Nextly, the method of the invention is described by making reference to the accompanying drawing illustrating the method consisting of the known method illustrated in FIG. 1 and a detector cell-cleaning treatment in combination.

Figure 2:
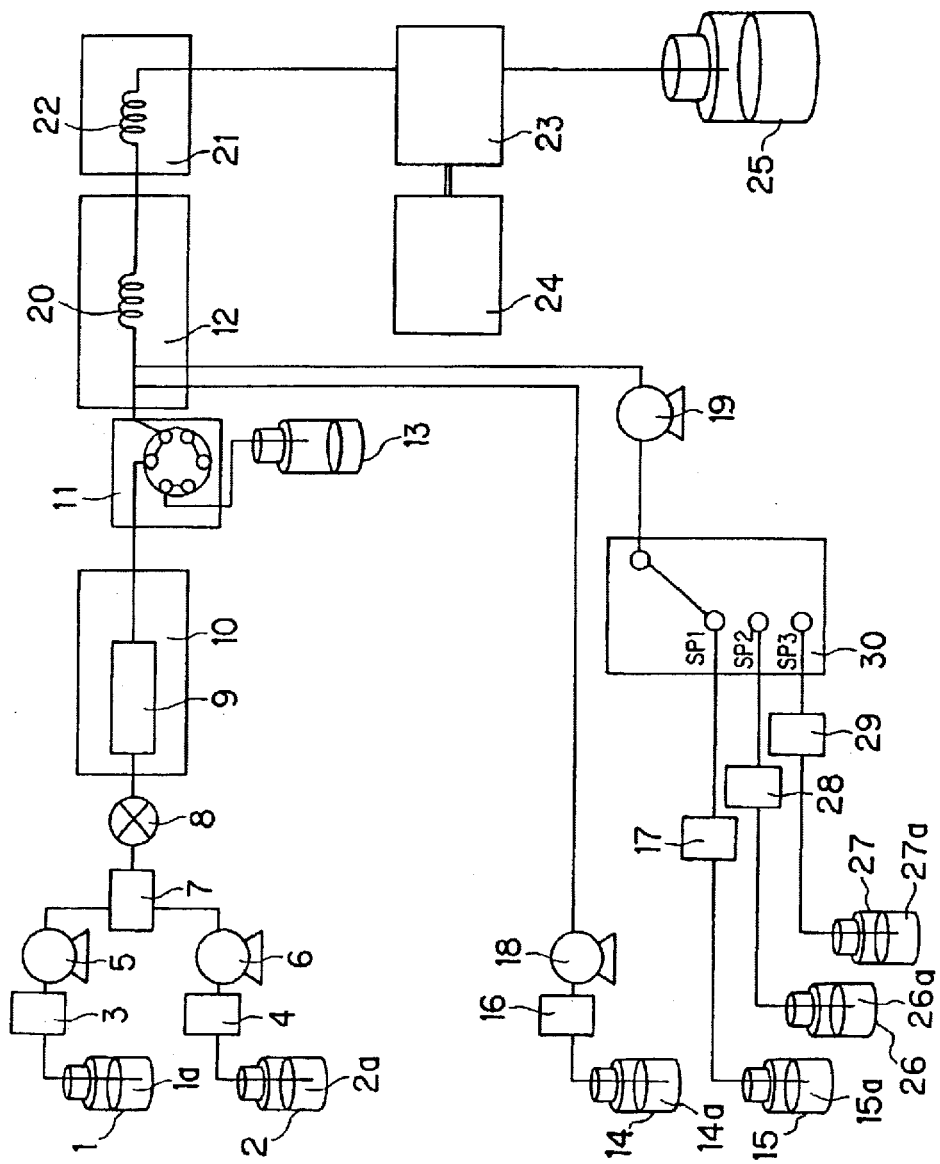
FIG. 2 is a full flow chart of the inventive method.

FIG. 2 shows a flow chart of the inventive method as a whole, which comprises solvent reservoirs 1,2 for the mobile phases, degassing apparatuses 3,4, liquid-feed pumps 5,6 and a mixer 7. When the elution is conducted as a gradient elution method, the mixer 7 serves in mixing of the solvent 1a transferred from the mobile-phase reservoir 1 by the pump 5 and the solvent 2a transferred from the mobile-phase reservoir 2 by the pump 6. The sample solution, i.e. saccharide mixture solution, injected at the sample injection valve 8 is introduced, by means of the mobile phase, into the analytical column 9 where the saccharide mixture is separated into the individual constituent saccharides. The analytical column is kept at a constant temperature in a thermostat 10. During the sample analysis, the eluate from the analytical column is transferred into the reaction vessel 12 by passing a flow channel-switching apparatus 11 for the eluate from the analytical column.

Figure 3:
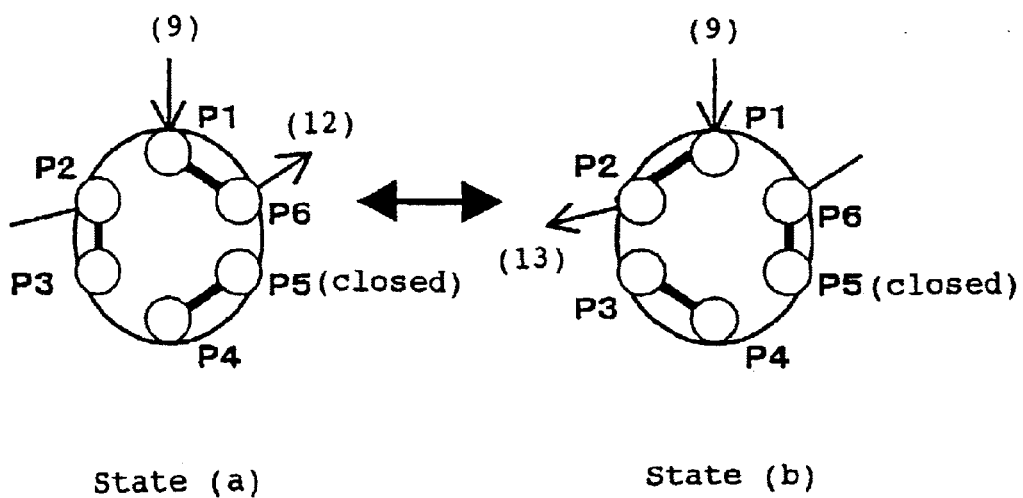
FIG. 3 is an explanatory illustration for the flow channel-switching mechanism in FIG. 2.

As is shown in FIG. 3, the flow channel-switching apparatus 11 is, during the sample analysis, held in a state (a) where a flow channel is established to allow the eluate from the analytical column introduced into the reaction vessel 12. During the interval from completion of a single run of the sample analysis to the start of the detector cell-cleaning treatment, switching is conducted in the flow channel-switching apparatus 11 to establish a state (b) in which the flow channel of the eluate is led toward the waste reservoir 13 with interruption of the flow channel to the reaction vessel 12. During the interval from completion of the detector cell-cleaning treatment to the injection of the next sample solution, the flow channel is again switched by means of the flow channel-switching apparatus 11 so as to resume the state (a) where the eluate from the analytical column is led to the reaction vessel 12.

The apparatus system of the invention further comprises reservoirs 14,15 for the reagents to convert the separated constituent saccharides into respective derivatives thereof, degassing apparatuses 16,17 for degassing the reagent solutions 14a,15a in the reagent reservoirs 14,15 and liquid-feed pumps 18,19 for transferring the reagent solutions 14a,15a in the reagent reservoirs 14,15.

It is usual that a plurality of the reagent reservoirs are provided in order to enable replacement of the reagent solutions depending on the individual saccharides to be converted to the derivatives. Each of the constituent saccharides separated in the analytical column 9 is mixed with the reagent solution and converted into a derivative thereof during passage through a reaction coil 20 within the reaction vessel 12. The derivative is cooled by passing a cooling coil 22 kept at a constant temperature in a cooling vessel 21 and then introduced into a detector cell of the detector 23 to be detected there. The detector signals are processed in a data-processing unit 24. The waste solution flowing out of the detector 23 is collected in the waste reservoir 25.

The detector cell-cleaning solvents 26a,27a are contained in the cleaning solvent reservoirs 26,27. The cleaning solvents 26a,27a in the reservoirs 26,27 are subjected to a degassing treatment in the degassing apparatuses 28,29.

The flow channel-switching apparatus 30 between the reagent solution and the cleaning solvent is an apparatus for selectively connecting one of the three flow channel positions including the flow channel position SP1 in FIG. 2 connecting the reagent reservoir 15 to the liquid-feed pump 19 via the degassing apparatus 17, the flow channel position SP2 in FIG. 2 connecting the cleaning solvent reservoir 26 to the liquid-feed pump 19 via the degassing apparatus 28 and the flow channel position SP3 in FIG. 2 connecting the cleaning solvent reservoir 27 to the liquid-feed pump 19 via the degassing apparatus 29.

The flow channel-switching apparatus 30 between the reagent solutions and the cleaning solvents is, during the sample analysis, in the flow channel position SP1 where the reagent reservoir 15 is connected to the pump 19 via the degassing apparatus 17 so as to transfer the reagent solution 15a from the pump 19. During the interval from completion of the analysis for a single sample to the start of the detector cell-cleaning treatment, switching of the flow channels is undertaken by means of the flow channel-switching apparatus 30 so as to disconnect the flow channel connecting the reagent reservoir 15 to the pump 19 via the degassing apparatus 17 and, instead, to establish either one of the flow channel connecting the cleaning solvent reservoir 26 to the pump 19 via the degassing apparatus 28 and the flow channel connecting the cleaning solvent reservoir 27 to the pump 19 via the degassing apparatus 29 enabling liquid transfer of the cleaning solvent 26a or 27a by means of the pump 19.

In conducting the detector cell-cleaning treatment by using two or more different detector cell-cleaning solvents, switching of the flow channel from a cleaning solvent to another is carried out by means of the flow channel switching apparatus 30. During the interval from completion of the detector cell-cleaning treatment to the next sample injection, switching of the flow channels is undertaken by means of the flow channel switching apparatus 30 to resume the flow channel position SP1 connecting the reagent reservoir 15 to the pump 19 via the degassing apparatus 17 enabling transfer of the reagent solution 15a by the pump 19. While FIG. 2 illustrates the process in which the detector cell-cleaning treatment is conducted by using two different cleaning solvents 26a,27a, it is sometimes the case that full cell cleaning effect can be obtained by using a single cleaning solvent.

In the case of immiscibility of the solution in the detector cell at a moment of completion of the analysis of a single sample or the reagent solution 15a with the detector cell-cleaning solvent, it is necessary that the detector cell is subjected to a cleaning treatment with a solvent having miscibility with both of the solution in the detector cell at the moment of completion of the analysis or the reagent solution 15a and the detector cell-cleaning solvent and that, after switching of the flow channels, the detector cell is subjected to cleaning with the detector cell-cleaning solvent. In this case, either one of the cleaning solvent reservoirs 26,27 is used as a substitution solvent reservoir containing the solvent used for replacement within the detector cell and the flow channels. It is optional that an additional flow channel switching apparatus is inserted between the degassing apparatus 16 and the liquid-feed pump 18 which is equivalent to the flow channel switching apparatus 30 and an additional cleaning solvent reservoir containing the same cleaning solvent as the cleaning solvents 26a,27a is added therebetween so that the detector cell-cleaning treatment can be conducted by using the pumps 18,19.

While the above example is given for dual installation of the reservoirs for the solvents to be used as the mobile phase, the reagent reservoirs and the detector cell-cleaning solvents, it is of course possible to provide three or more units for each of these devices enabling use of three or more different mobile phase solvents, reagent solutions and detector cell-cleaning solvents.

In the following, the method of the present invention is described in more detail by way of an Example and Comparative Examples, which, however, never limit the scope of the invention in any way.

EXAMPLE

In FIG. 2, a solvent mixture of acetonitrile and distilled water in a volume ratio of 79:21 was used as the solvent 1a, a 1.0M aqueous solution of potassium hydroxide was used as the reagent solution 14a, a solution prepared by dissolving 100 mM of benzamidine hydrochloride monohydrate in a 40:60 by volume mixture of acetonitrile and distilled water was used as the reagent solution 15a, distilled water was used as the cleaning solvent of the detector cell 26a and acetonitrile of 98 mass % minimum was used as the detector cell cleaning solvent 27a.

An on-line degassing apparatus (manufactured by Tosoh Co.) was used as the degassing apparatuses 3,4,16,17,28,29 for removal of the dissolved gases in the respective solutions.

A liquid-feed pump Model CCPM-II (manufactured by Tosoh Co.) was used as the liquid-feed pumps 5,6 for feeding the mobile phase to conduct high-pressure gradient elution with the solvent 1a and solvent 2a under control by a Model PX-8020 pump controller. A liquid-feed pump Model CCPM-II, resin-finish (manufactured by Tosoh Co.) was used as the liquid-feed pumps 18,19 for feeding the reagent solution and the cleaning solvent under control by a Model PX-8020 pump controller. A dynamic mixer Model MX-8010 (manufactured by Tosoh Co.) was used as the mixer 7. The sample solution used was a solution containing ribose (2.0 μg/ml), fructose (2.0 μg/ml), glucose (2.0 μg/ml), laminaribiose (2.0 μg/ml), laminaritriose (2.0 μg/ml), laminaritetraose (2.0 μg/ml), laminaripentaose (2.0 μg/ml), laminarihexaose (2.0 μg/ml) and laminariheptaose (2.0 μg/ml). A 10 μl portion of this solution was injected through the sample injection valve 8 of the sample injection apparatus which was a Model AS-8020 Autosampler (manufactured by Tosoh Co.). The analytical column 9 employed was a Model TSKgel Amide-80 column (a product by Tosoh Co.) having an inner diameter of 4.6 mm and a length of 25 cm, which was set in a thermostat 10 controlled at a temperature of 80° C. The thermostat 10 was a column thermostat Model CO-8020 manufactured by Tosoh Co.

In conducting elution, the column was equilibrated in advance before injection of the sample solution by feeding the solvent 1a which occupied 100% volume of the mobile phase. Immediately after injection of the sample solution, mixing of the solvent 2a was started and the concentration of the solvent 2a in the mobile phase was linearly increased with lapse of time reaching 100% concentration of the solvent 2a in the mobile phase after 35.0 minutes from injection of the sample solution. Namely, the elution was conducted by the method of linear-gradient concentration-increasing elution, referred to as the gradient elution method.

After lapse of 35.0 minutes from injection of the sample solution, feeding of the mobile phase was continued keeping a 100% proportion of the solvent 2a in the mobile phase. The feed rates were set at 0.8 ml/minute for the mobile phase, at 0.6 ml/minute for the reagent solution 14a and at 0.6 ml/minute for the reagent solution 15a. The derivative-forming reaction of the respective constituent saccharides separated in the column 9 was conducted in a stainless steel-made reaction coil 20 having an inner diameter of 0.4 mm and a length of 20 m and placed in a reaction vessel 12. The reaction vessel 20 used was a Model RE-8020 reaction vessel (manufactured by Tosoh Co.), which was thermostatted at a constant temperature of 95° C.

The reaction mixture coming out of the reaction coil 20 was cooled by passing a Teflon-made cooling coil 22 having an inner diameter of 0.25 mm and a length of 4 m and placed in a thermostat 21 followed by detection of the reaction product in a fluorescence detector 23. A Model LCH-2000 cooling tank (manufactured by Advantec Toyo Co.) was used as the thermostat 21 which was controlled at a constant temperature of 9° C. The flow channel-switching apparatus 11 for the eluate from the analytical column, which was mounted between the analytical column 9 and the reaction tank 12, was a Model VC-8020 Valve Controller (manufactured by Tosoh Co.) equipped with a switching valve unit.

By using the flow channel-switching apparatus 11 for the eluate from the analytical column, the eluate from the analytical column was introduced into the reaction coil 12 when analysis of the sample was under way [noted as state (a) in FIG. 3] and the eluate from the analytical column was discharged to the waste reservoir 13 when the detector cell-cleaning treatment was under way [noted as state (b) in FIG. 3] by switching the eluate flow channels. The data-recording time and the time interval from completion of an analytical procedure to the injection of the next sample solution were set at 50 minutes and at 40 minutes, respectively, while sample injection was carried out in every 90 minutes. The detector cell was subjected to cleaning each time after completion of the single analytical procedures of the samples.

The flow channel-switching apparatus 30 for the reagent solution and the cleaning solvent to be installed between the liquid-feed pump 19 and the degassing apparatus 17 used here was a Model VC-8020 Valve Controller equipped with a solenoid valve unit manufactured by Tosoh Co. By using the flow channel-switching apparatus 30 for the reagent solution and the cleaning solution, the reagent solution 15a was transferred by means of the liquid-feed pump 19 when sample analysis was under way (noted as flow channel position SP1 in FIG. 2) and the cleaning solution 26a (noted as flow channel position SP2 in FIG. 2) or 27a (noted as flow channel position SP3 in FIG. 2) was transferred during the step of detector cell cleaning by switching the flow channels.

The detector cell-cleaning treatment was conducted by first introducing the detector cell-cleaning solvent 26a for 2.8 minutes at a flow rate of 2.0 ml/minute, then the detector cell-cleaning solvent 27a for 15 minutes at a flow rate of 2.0 ml/minute and finally the cell cleaning solvent 26a for 3 minutes at a flow rate of 2.0 ml/minute. Immediately after start of the detector cell-cleaning treatment, a re-equilibration treatment of the analytical column was started by switching the mobile phase to the solvent 1a alone, i.e. the mobile phase at the start of the analysis. This re-equilibration treatment with the solvent 1a alone as the mobile phase was continued until injection of the next sample solution.

The detector 23 used here was a Model FS-8020 Fluorescence Detector manufactured by Tosoh Co. and the data processor 24 was a Model LC-8020 Date Processor manufactured by Tosoh Co. Table 1 below summarizes the liquid-feed control factors such as the feed rate in each of the solvent-feed pumps 5,6,18,19 and the control programs of the flow channel-switching apparatus 11 for the eluate from the analytical column and the flow channel-switching apparatus 30 for the reagent solutions and cleaning solvents for the 90 minutes interval from start of the analysis.

In this table, each of the solvents transferred and the flow rate thereof are indicated within the square brackets [ ] and round brackets ( ). The flow rate in the mobile phase-transfer pumps was set constant at 0.8 ml/minute and the data recording time was 50 minutes from injection of the sample solution with a 40 minutes interval between completion of an analytical procedure and injection of the next sample solution. The detector cell was cleaned after completion of each of the analytical procedures.

Figure 4:
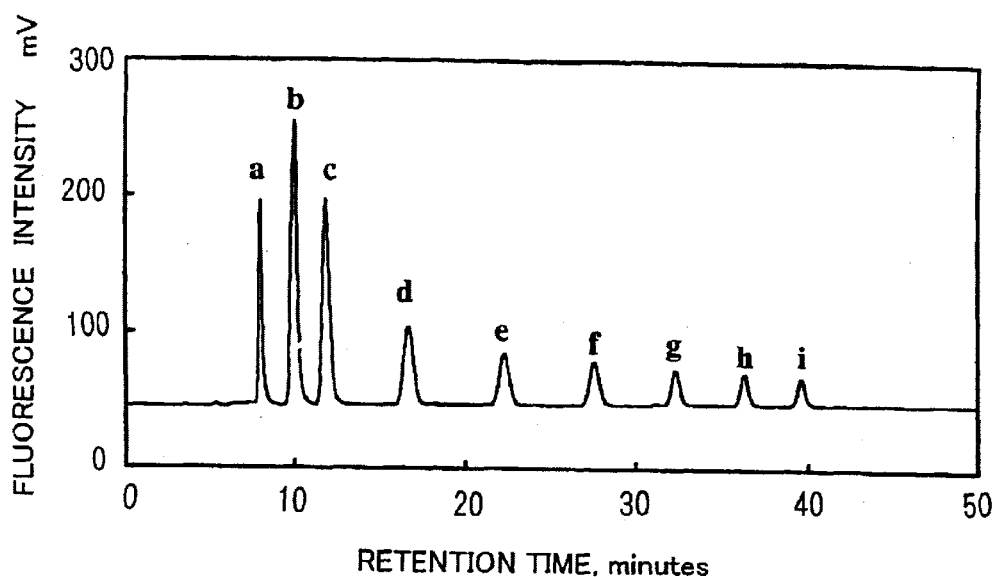
FIG. 4 is a chromatogram showing an analytical result obtained in Example of the inventive method.

A single sample was subjected to 12 times of consecutive analytical procedures according to the analytical program indicated. FIG. 4 shows a part of the chromatograms obtained in this manner, in which the peaks indicated by the symbols a, b and c correspond to the monosaccharides including ribose, fructose and glucose, respectively, and the peaks indicated by d, e, f, g, h and i correspond to the oligosaccharides including laminaribiose, laminaritriose, laminaritetraose, laminaripentaose, laminarihexaose and laminariheptaose, respectively.

As is shown in FIG. 4, separation of each monosaccharide from the other monosaccharides and each oligosaccharide from the other oligosaccharides was complete. The overall time taken for complete elution of these saccharides was 45 minutes or shorter. Table 2 below shows the values of the retention times of the saccharide peaks in minutes and peak heights, i.e. fluorescence intensities in mV obtained by 12 times repeated analysis of glucose and laminaribiose among the reducing saccharides subjected to the analysis.

The coefficients of variation CV (relative standard deviation) for the retention time with regard to glucose and laminaribiose were 0.116% and 0.143%, respectively, and the coefficients of variation CV for the fluorescence peak height thereof were 0.860% and 1.14%, respectively. The coefficient of variation CV (relative standard deviation) here was a quotient value of the standard deviation S ($S=\sigma_{n-1}$) for the sample divided by the average value x for the sample as multiplied by a factor 100. It is understood from the above given results that, according to the inventive method, high-sensitivity detection can be accomplished of a saccharide sample containing monosaccharides and oligosaccharides and with good resolution among monosaccharides and complete elution of oligosaccharides within a short time. Further, the results of the coefficient of variation CV indicate reproducibility of the analytical values to be obtained in repeated analyses.

TABLE 1

| Time, minutes | Apparatus, numerical sign in FIG. 2 | Explanation [solvent] (flow rate) |
|---|---|---|
| State: ready for analysis | Mobile phase-transfer pump 5, 6 | [solution 1a 100.0%] (flow rate 0.8 ml/min.) |
| | Pump 18 | [14a] (flow rate 0.6 ml/min.) |
| | Pump 19 | [15a] (flow rate 0.6 ml/min.) |
| | Flow channel-switching apparatus 11 | State a |
| | Flow channel-switching apparatus 30 | Flow channel position SP1 |
| | Detector 23 | Zero-point calibration of detector completed |
| 0.0 | Sample injection apparatus 8 | First injection of sample solution |
| | Data-processing unit 24 | Data-recording for first sample solution started |
| | 5, 6 | Gradient elution started, linear concn. increase of 2a, [1a 100%] to [2a 100%] during 35.0 mins. |
| | 18 | [14a] (flow rate 0.6 ml/min.) |
| | 19 | [15a] (flow rate 0.6 ml/min.) |
| | 11 | State a |
| | 30 | Flow channel position SP1 |
| 35.0 | 5, 6 | Completion of gradient elution |
| | 5, 6 | [2a 100.0%] |
| 50.0 | 24 | Completion of data-recording for first sample solution |
| 50.1 | 18 | [14a] Stopping of liquid feeding |
| | 11 | Switching from state a to state b |
| | 30 | Flow channel position switched from SP1 to SP2 |
| 50.2 | 19 | [26a] (Flow rate changed from 0.6 to 2.0 ml/min.) |
| | 5, 6 | Re-equilibration at [1a 100.0%] |
| 53.0 | 30 | Flow channel position switched from SP2 to SP3 |
| | 19 | [27a] (flow rate 2.0 ml/min.) |

TABLE 1-continued

| Time, minutes | Apparatus, numerical sign in FIG. 2 | Explanation [solvent] (flow rate) |
|---|---|---|
| 68.0 | 30 | Flow channel position switched from SP3 to SP2 |
|  | 19 | [26a] (flow rate 2.0 ml/min.) |
| 71.0 | 30 | Flow channel position switched from SP2 to SP1 |
|  | 19 | [15a] (flow rate changed from 0.6 to 2.0 ml/min.) |
|  | 18 | [14a] Liquid feed resumed (flow rate 0.6 ml/min.) |
| 80.0 | 11 | Switching from state b to state a |
| 89.0 | 23 | Zero point calibration |
| 90.0 | 8 | Second sample solution injected |
|  | 24 | Data-recording for second sample solution started |
|  | 5, 6 | Gradient elution started, linear concn. increase of 2a, [1a 100%] to [2a 100%] during 35.0 mins. |

TABLE 2

| Times of analysis | Retention time, minutes | | Peak height, mV | |
|---|---|---|---|---|
|  | Glucose | Laminaribiose | Glucose | Laminaribiose |
| 1 | 11.891 | 16.732 | 150.770 | 57.397 |
| 2 | 11.891 | 16.757 | 150.192 | 56.416 |
| 3 | 11.891 | 16.757 | 152.981 | 56.305 |
| 4 | 11.899 | 16.766 | 149.885 | 55.689 |
| 5 | 11.899 | 16.766 | 149.410 | 57.242 |
| 6 | 11.907 | 16.782 | 152.031 | 56.332 |
| 7 | 11.924 | 16.807 | 149.315 | 55.911 |
| 8 | 11.874 | 16.724 | 149.315 | 55.441 |
| 9 | 11.874 | 16.732 | 151.958 | 57.327 |
| 10 | 11.891 | 16.732 | 150.171 | 56.646 |
| 11 | 11.882 | 16.749 | 148.715 | 56.041 |
| 12 | 11.891 | 16.749 | 150.313 | 56.004 |
| Average value | 11.893 | 16.754 | 150.421 | 56.396 |
| Coefficient of variation | 0.116% | 0.143% | 0.860% | 1.14% |

Comparative Example 1

The analytical procedure as in Example 1 was consecutively repeated 12 times for the same sample as in Example by using the same apparatus as in Example excepting for omission of the detector cell-cleaning treatment. The flow channel-switching apparatus 11 for the eluate from the analytical column was fixed to the state (a) and the flow channel-switching apparatus 30 for the reagent solution and cleaning solvent was fixed to the flow channel position SP1. The mobile phase solvent 1a, mobile phase solvent 2a, reagent solution 14a and reagent solution 15a were each the same one as used in Example. The mobile phase-transfer pumps 5,6 were controlled with the same program as in Example to introduce the mobile phase at a flow rate of 0.8 ml/minute (see Table 1). During the consecutive analyses, the flow rates of the reagent solution 14a and reagent solution 15a were kept each at 0.6 ml/minute. The other analytical conditions were the same as in Example. Table 3 below shows the peak heights (fluorescence intensity, mV) for glucose and laminaribiose among the reducing saccharides tested.

The coefficients of variation Cv (relative standard deviations) for the fluorescence peak heights with regard to glucose and laminaribiose were 3.65% and 4.58%, respectively. Namely, the coefficients of variation CV in this case with omission of the detector cell-cleaning treatment for glucose and laminaribiose were 4.2 times and 4.0 times, respectively, of the values of coefficient of variation in Example indicating higher reproducibility of the analytical results.

Thus, it is clear that the reproducibility of the analytical values in Comparative Example 1 with omission of the detector cell-cleaning treatment was definitely lower than in Example.

TABLE 3

| Times of analysis | Peak height, mV | |
|---|---|---|
|  | Glucose | Laminaribiose |
| 1 | 151.993 | 56.522 |
| 2 | 152.851 | 57.598 |
| 3 | 149.934 | 56.259 |
| 4 | 149.351 | 55.941 |
| 5 | 151.489 | 57.056 |
| 6 | 149.650 | 56.004 |
| 7 | 146.785 | 55.604 |
| 8 | 145.150 | 54.422 |
| 9 | 144.290 | 52.570 |
| 10 | 141.444 | 52.669 |
| 11 | 138.620 | 50.896 |
| 12 | 136.726 | 50.029 |
| Average value | 146.524 | 54.631 |
| Coefficient of variation | 3.65% | 4.58% |

Comparative Example 2

The same sample as in Example was subjected to 12 times repeated consecutive analysis by using the same apparatus as used in Example (FIG. 2) by conducting cleaning of the detector cell with dismounting of the analytical column for the purpose of cell cleaning after analysis of each sample instead of conducting flow channel-switching of the eluate from the analytical column by means of the flow channel-switching apparatus in the detector cell-cleaning treatment in Example. The flow channel-switching apparatus 11 for the eluate from the analytical column was fixed to the state (a) and the flow channel-switching apparatus 30 for the reagent solution and the cleaning solvent was fixed to the flow channel position SP1.

The mobile phase solvent 1a, mobile phase solvent 2a and reagent solutions 14a and 15a used here were each the same one as in Example. The mobile phase-transfer pumps 5,6 were controlled with the same program as in Example. The flow rate of the mobile phase was 0.8 ml/minute (see Table 1). During the consecutive analyses, the flow rates of the reagent solution 14a and the reagent solution 15a were each kept at 0.6 ml/minute.

The detector cell-cleaning treatment was conducted in the following manner. When data recording was completed after lapse of 50.0 minutes from injection of the sample solution, all of the liquid-feed pumps were stopped and the analytical column was dismounted and replaced with a stainless steel tube to conduct a cleaning treatment of the detector cell. The detector cell-cleaning treatment was carried out by feeding first the detector cell-cleaning solvent 26a for 2.8 minutes, then the detector cell-cleaning solvent 27a for 15 minutes and finally the detector cell-cleaning solvent 26a for 3 minutes each at a flow rate of 2.0 ml/minute.

After the detector cell-cleaning treatment, the stainless steel tube was replaced with the analytical column and the cleaning solvent was switched to the mobile phase solvent 1a alone which was transferred by means of the liquid-feed pumps 5,6 along with resumption of liquid feedings of the reagent solution 14a by means of the liquid-feed pump 18 and the reagent solution 15a by means of the liquid-feed pump 19. After a re-equilibration treatment of the analytical column taking 30 minutes with the mobile phase used in the initial equilibration, i.e. the mobile phase at the start of analysis, injection of the next sample solution was undertaken. The other analytical conditions were the same as in Example. Table 4 below shows the retention times in minutes for glucose and laminaribiose among the reducing saccharides tested.

The coefficients of variation CV (relative standard deviations) relative to the retention times in minutes for glucose and laminaribiose were 0.157% and 0.244%, respectively. These CV values for glucose and laminaribiose obtained in this Comparative Example 2, which involved dismounting of the analytical column during the detector cell-cleaning treatment or, namely, repetition of stopping and re-starting of the liquid feed-pumps for the mobile phase during the consecutive analyses, were 1.4 times and 1.7 times, respectively, of the corresponding CV values in Example indicating less reproducibility of the analytical results.

It is understood from the above-given results that, as compared with Example, the reproducibility of the analytical values is decreased in this Comparative Example 2 which involved dismounting of the analytical column in the course of the detector cell-cleaning treatment or, namely, repetition of stopping and re-starting of the liquid feed-pumps for the mobile phases. This procedure took about 55 minutes of time including about 5 minutes for the dismounting and mounting works of the analytical column, about 20.8 minutes for the detector cell-cleaning treatment and about 30 minutes for the re-equilibration treatment of the analytical column with the mobile phase for the initial equilibration of the analytical column so that the interval between two consecutive sample injections was about 105 minutes. These results indicated that the number of the samples which could be analyzed in consecutive analyses within a prescribed time is necessarily small as compared with Example.

TABLE 4

| Times of analysis | Retention time, minutes | |
| --- | --- | --- |
| | Glucose | Laminaribiose |
| 1 | 11.911 | 16.771 |
| 2 | 11.885 | 16.846 |
| 3 | 11.877 | 16.755 |
| 4 | 11.902 | 16.738 |
| 5 | 11.861 | 16.705 |
| 6 | 11.886 | 16.697 |
| 7 | 11.911 | 16.747 |
| 8 | 11.902 | 16.755 |
| 9 | 11.877 | 16.713 |
| 10 | 11.919 | 16.771 |
| 11 | 11.877 | 16.705 |
| 12 | 11.869 | 16.747 |
| Average value | 11.890 | 16.746 |
| Coefficient of variation | 0.157% | 0.244% |

Comparative Example 3

Figure 5:
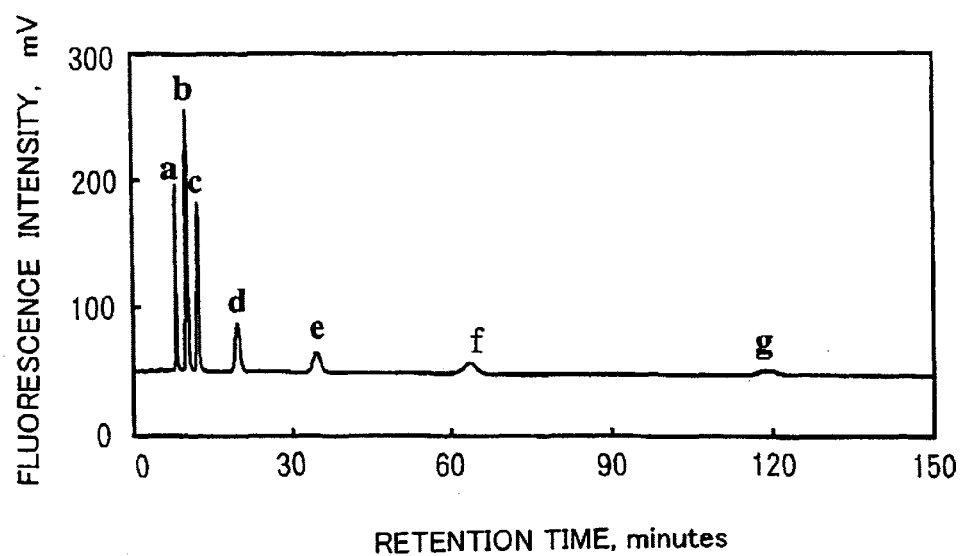
FIG. 5 is a chromatogram showing the analytical result obtained in Comparative Example 3.

Analysis was undertaken by the same elution method as in Example excepting for the use of a mobile phase of a single formulation instead of the use of two kinds or more of the eluants. Namely, the mobile phase of the single formulation was a 79:21 by volume mixture of acetonitrile and distilled water. FIG. 5 shows a chromatogram obtained in this elution, in which, although monosaccharides could be separated each from the others, complete elution of the oligosaccharides could not be accomplished because of ending of the analysis time of 150 minutes with elution of laminaripentaose and no more. It is understood therefore that high resolution among monosaccharides and complete elution of oligosaccharides within a short time are incompatible in this Comparative Example 3 by using a single kind of the mobile phase.

Comparative Example 4

Figure 6:
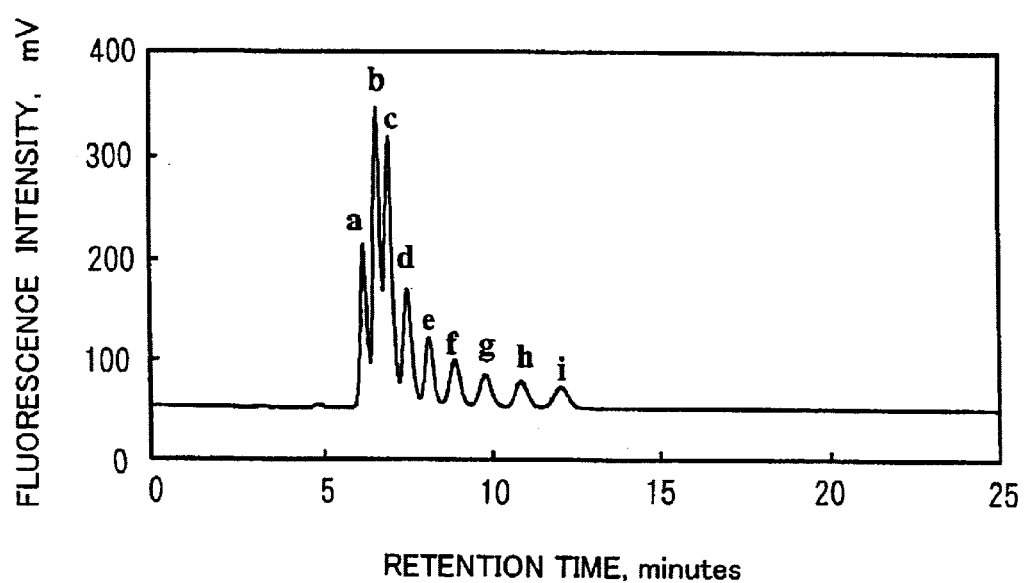
FIG. 6 is a chromatogram showing the analytical result obtained in Comparative Example 4.

Analysis was conducted in the same manner as in Example except that the elution method of Example was carried out by using a mobile phase of a single formulation instead of the use of two kinds or more of the eluants. The mobile phase of the single formulation used here was a 58:42 by volume mixture of acetonitrile and distilled water. FIG. 6 shows a chromatogram obtained in this manner. It was understood therefrom that, although elution of the oligosaccharides could be accomplished to laminariheptaose within 15 minutes, resolution among the monosaccharides could not be accomplished. Accordingly, it was concluded that high resolution among the monosaccharides and complete elution of the oligosaccharides within a short time were incompatible without difficulties in this Comparative Example 4 by using a single kind of the mobile phase.

What is claimed is:

1. A method for simultaneous analysis of a saccharide mixture comprising monosaccharides, oligosaccharides or a combination thereof by a liquid chromatographic method using at least two different mobile phases, which method comprises the steps of:

(a) separating the monosaccharides and oligosaccharides by the liquid chromatography by using an analytical column into individual saccharides (b) in a reactor coupled to the analytical column reacting each of the separated saccharides with a reagent to convert the saccharide into a derivative thereof detectable by a detecting method;

(c) introducing the derivatives of the saccharides consecutively into a detector cell coupled to the reactor;

(d) detecting the saccharide derivatives in the detector cell consecutively by the detecting method;

(e) cleaning the detector cell with a detector cell-cleaning solvent each time after completion of the consecutive detection of the saccharide derivatives by flowing the cell-cleaning solvent from a resolve coupled to the detector cell; and (f) a step for a re-equilibration treatment of the analytical column, the re-equilibration treatment of the analytical column being conducted simultaneously with cleaning of the detector cell by shutting off a flow channel connecting the detector cell and the analytical column, passing a mobile phase for equilibration of the analytical column through the analytical column to waste reopening and the flow channel after said shutting off the flow channel and prior to loading of the analytical column with a subsequent solution of the saccharide mixture.

2. An apparatus system for use in a method for simultaneous analysis of a saccharide mixture comprising monosaccharides, oligosaccharides or a combination thereof by a liquid chromatographic method using at least two different mobile phases, which method comprises the steps of:

(a) separating the monosaccharides and oligosaccharides by the liquid chromatography by using an analytical column into individual saccharides:

(b) in a reactor coupled to the analytical column reacting each of the separated saccharides with a reagent to convert the saccharide into a derivative thereof detectable by a detecting method;

(c) introducing the derivatives of the saccharides consecutively into a detector cell coupled to the reactor;

(d) detecting the saccharide derivatives in the detector cell consecutively by the detecting method;

(e) cleaning the detector cell with a detector cell-cleaning solvent each time after completion of the consecutive detection of the saccharide derivatives by flowing the cell-cleaning solvent from a reservoir coupled to the detector cell, and (f) a step for a re-equilibration treatment of the analytical column, the re-equilibration treatment of the analytical column being conducted simultaneously with cleaning of the detector cell by shutting off a flow channel connecting the detector cell and the analytical column, passing a mobile phase for equilibration of the analytical column through the analytical column to waste reopening and the flow channel after said shutting off the flow channel and prior to loading of the analytical column with a subsequent solution of the saccharide mixture which apparatus system comprises:

(A) an analytical column of liquid chromatoghraphy for separating the saccharide mixture into the individual saccharides;

(B) coupled to the analytical column a reactor for reacting each of the separated saccharides with a reagent to convert the saccharide into a derivative thereof detectable by a detecting method;

(C) coupled to the reactor a detector cell for containing the saccharide derivative;

(D) a detector means for detecting the saccharide derivative contained in the detector cell;

(E) coupled to the detector cell a means for introducing a detector cell-cleaning solvent into the detector cell each time after completion of the consecutive detection of the saccharide derivatives;

(F) coupled to the analytical column a means for regeneration of the analytical column; and (G) a means for switching a flow channel of the eluate from the analytical column between a first state in which the eluate flows to the detector and a second state in which the eluate flows to waste;

where in the means for introducing and the means for regeneration operates simultaneously.

3. The apparatus system as claimed in claim 2 in which the means (G) comprises a mechanism for shutting off the flow channel connecting the analytical column and the detector cell and a mechanism for reopening the flow channel of the eluate after shutting off the flow.

* * * * *

UNITED STATES PATENT AND TRADEMARK OFFICE
CERTIFICATE OF CORRECTION

PATENT NO. : 6,855,555 B2
DATED : February 15, 2005
INVENTOR(S) : Hirotaka Kakita et al.

It is certified that error appears in the above-identified patent and that said Letters Patent is hereby corrected as shown below:

Column 16,
Line 34, please replace "saccharides" with -- saccharides; --.
Line 35, please replace "column reacting" with -- column, reacting --.
Line 46, please replace "resolve" with -- reservoir --.
Lines 54 and 55, please replace "waste reopening and" with -- waste and reopening --.

Column 17,
Line 1, please replace "column reacting" with -- column, reacting --.
Lines 21 and 22, please replace "waste reopening and" with -- waste and reopening --.

Column 18,
Line 1, please replace "column a reactor" with -- column, a reactor --.
Line 5, please replace "reactor a detector" with -- reactor, a detector --.
Line 9, please replace "cell a means" with -- cell, a means --.
Line 13, please replace "column a means" with -- column, a means --.
Line 26, please replace "after shutting" with -- after said shutting --.

Signed and Sealed this

Seventeenth Day of May, 2005

JON W. DUDAS
*Director of the United States Patent and Trademark Office*